United States Patent [19]

Pichierri

[11] 4,007,263
[45] Feb. 8, 1977

[54] STOMA TREATMENT

[76] Inventor: Virgil F. Pichierri, 53 Brigham Hill Road, Grafton, Mass. 01519

[22] Filed: Mar. 25, 1975

[21] Appl. No.: 561,851

Related U.S. Application Data

[63] Continuation of Ser. No. 387,332, Aug. 10, 1973, abandoned.

[52] U.S. Cl. ................................................ 424/78
[51] Int. Cl.$^2$ ...................................... A61K 31/74
[58] Field of Search .................................... 424/78

[56] References Cited

UNITED STATES PATENTS 3,003,988  10/1961  Germann et al. ................. 260/33.6

*Primary Examiner*—Stanley J. Friedman
*Attorney, Agent, or Firm*—Norman S. Blodgett; Gerry A. Blodgett

[57] ABSTRACT

A method of relieving skin irritation surrounding an iliac stoma established after an ileostomy or colostomy (surgical removal of the intestine), the method involving local application of a paste containing calcium, sodium poly (vinyl methyl ethermaleate) in a petrolatum base.

4 Claims, No Drawings

STOMA TREATMENT

This is a continuation of application Ser. No. 387,332 filed 10 Aug. 1973, now abandoned.

BACKGROUND OF THE INVENTION

Certain intestinal malfunctions, especially cancer of the colon and chronic ulcerative colitis, require removal of portions of the intestine. If large portions must be removed, an alternative passage for fecal excretion must be provided. The normal procedure is to form a permanent opening in the abdomen of the patient and to extend the open end of the small intestine through the opening to the outside of the body. The portion of the intestine which extends outward from the skin is called an iliac stoma. To capture the exiting feces, a bag is placed over the end of the stoma.

Along with the considerable physiological and psychological problems inherent in such a long-time prosthesis, the additional problem of intense skin excoriation or irritation around the stoma is common. Such irritation is caused by inevitable leakage of gastric acid and fecal drainage and can detract considerably from the patient's ability to lead a normal life.

Although modern medicine has done much to relieve the irritation in certain cases, the problem has, by no means been solved. In a typical case, a patient suffered with the immobilizing irritation for eleven years while trying a veitable pharmacopoeia of preparations.

Various conventional preparations were applied to the area of extensive burns, inflamation and marked eroded ulcers, surrounding the stoma.

One preparation contained Benzocain, zinc oxide, and oxyquinoline sulfate menthol in a petrolatum base. After application, the irritation would sting for a few seconds. The preparation would not adhere to the weeping skin. The anesthetic effect would last only momentarily and the preparation was quickly attacked and desolved by the fecal drainage. Upon continued application, a sensitivity to the skin would develop and the substance would actually aggrevate the inflamed area, causing the eroded ulceration to bleed.

Various other standard ointments and creams, containing vitamins A and D and silicones, were tried. All these preparations caused increased inflamation. Various steroid preparations, sometimes effective in analogous situations, caused increased inflamation and unbearable burning pain. These and other difficulties experienced with the prior art devices have been obviated in a novel manner by the present invention.

It is, therefore, an outstanding object of the invention to provide a method of treating certain skin excoriations which is quickly effective to relieve the condition without undesirable side effects.

Another object of this invention is the provision of a method of treating certain skin excoriations, the method involving a preparation which is inexpensive to manufacture and has a long shelf-life without special handling.

With the foregoing and other objects in view which will appear as the description proceeds, the invention resides in the combination and arrangement of steps and the details of the composition hereinafter described and claimed, it being understood that changes in the precise embodiment of the invention herein disclosed may be made within the scope of what is claimed without departing from the spirit of the invention.

SUMMARY OF THE INVENTION

This invention involves the discovery that a certain chemical formulation, previously used as a denture adhesive, is useful in relieving skin irritation resulting from leakage at the site of an iliac stoma.

DESCRIPTION OF THE PREFERRED EMBODIMENT

In a practical application of the invention, a patient endured the skin excoriation for 11 years, while experimenting with all types of conventional and non-conventional protective creams and ointments. The following is an account of an experimental application of a calcium, sodium poly (vinyl methyl ether-maleate). The material is commercially available as a denture adhesive cream sold under the tradename "FIXODENT" by the Vick Chemical Company, Division of Richard-Merrel, Inc., New York, N. Y. 10017. The denture adhesive is manufactured as described in U.S. Pat. No. 3,003,988, issued on 10 Oct. 1961, to Donald P. Germann et al.

The results were as follows:

| Date | Observation |
|---|---|
| Nov. 3 | Skin before application of "Fixodent", highly irritated burn lesions and ulceration. |
| 9 a.m. | After application, pain subsided within 30 min. |
| 12:20 p.m. | Redness and swelling almost gone. |
| 9 p.m. | Ulcerations almost completely healed, redness and swelling gone. |
| Nov. 4 | Ulcerations, redness and swelling completely healed. Skin appears normal, new skin growth commencing. |
| Nov. 5 | Applied 4 times during day, skin still normal. |
| Nov. 6 | Applied 3 times during day, skin still normal, highly protected, no sensitivity. |
| Nov. 7 | Applied 3 times, normal, no sensitivity. |
| Nov. 8 | Applied 3 times, normal, no sensitivity. |
| Nov. 9 | Normal, no sensitivity. |
| Nov. 10 | Normal. |
| Nov. 11 | Normal. |
| Nov. 12 | Normal. |
| Nov.13 | Normal. |
| Nov. 14 | Normal. |
| Nov. 15 | Normal. |
| Nov. 16 | Normal, still no sensitivity. |
| Nov. 17 | Normal. |
| Nov. 18 | Normal. |
| Nov. 19 | Normal |
| Nov. 20 | Normal |
| Nov. 21 | Normal, no sensitivity. |
| Nov.22 | Normal. |
| Nov. 23 | Normal. |
| Nov. 24 | Normal. |
| Nov. 25 | Normal, no sensitivity. |
| Nov. 26 | Normal. |
| Nov. 27 | Normal. |
| Nov. 28 | Normal. |
| Nov. 29 | Skin still normal, no sensitivity. Substance highly resistant to fecal drainage and digestive acid, holds to skin. |
| Nov. 30 | Normal. |
| Months of December and January, skin still normal, highly protected against fecal drainage and irritation. Still no sensitivity. | |

The exact formulation and method of manufacture of the paste used in the present invention is described in the U.S. Pat. No. 3,003,988 cited above. Specifically the paste is an effective amount of at least 40 percent of a calcium, sodium poly (vinyl methyl ether-maleate) in a petroleum base. It is applied directly to the excoriated skin, three times daily.

While it will be apparent that the illustrated embodiments of the invention herein disclosed are well calculated adequately to fulfill the objects and advantages primarily stated, it is to be understood that the invention is susceptible to variation, modification, and change within the spirit and scope of the subjoined claims.

The invention having been thus described, what is claimed as new and desired to secure by Letters Patent is:

1. A method of relieving irritation of skin surrounding an iliac stoma; comprising the application to the skin, of a paste comprising an effective of at least 40 percent by weight of calcium, sodium poly(vinyl methyl ether-maleate) in a petroleum jelly base.

2. A method of relieving irritation of skin surrounding an iliac stoma comprising the application to the skin, of a paste having as a stabilizing component a material comprising an effective amount of at least 40 percent by weight of said paste and being a water-insoluble water-sensitized polymeric material; said material characterized by a particle size of minus 150-mesh U.S.B.S. sieve, by an apparent bulk density greater than 0.5 gram per cubic centimeter, and by a pH between 5 and 8.5, the pH being determined on a one percent by weight aqueous dispersion of said material in water; said material consisting essentially of a partial mixed salt of a copolymer selected from the group consisting of copolymers and partial lower alkyl esters of these copolymers, said copolymers consisting essentially of the repeated structural unit,

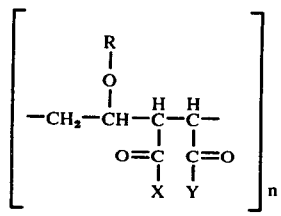

wherein X and Y separately each represent a hydroxyl radical and X and Y together represent a bivalent oxygen atom, R represents an alkyl radical of less than 5 carbon atoms, $n$ is an integer greater than one representing the number of repeated occurences of said structural unit in a molecule of said copolymer and $n$ is large enough to characterize said polymer as having a specific viscosity larger than 1.2, the specific viscosity being determined in methyl ethyl ketone at 25° C, said partial lower alkyl esters of said copolymer having less than one-third of the total initial carboxyl groups esterified, said partial mixed salts containing calcium cations and alkali cations, in a mole ratio of between 1:1 and 5:1, the alkali cations selected from the group consisting of sodium, potassium, and quaternary ammonium cations, with not more than one-third of the total initial carboxyl groups unreacted.

3. A method as recited in claim 2, wherein said water-insoluble water-sensitized polymeric material is dispersed in mineral oil and petrolatum jelly to provide cream-like composition.

4. A method as recited in claim 2, wherein the paste contains material of the particle size of minus 200-mesh U.S.B.S. sieve, of apparent bulk density having at least seven grams per cubic centimeter, and of pH between 6 and 7.

* * * * *